(12) United States Patent
Janssen et al.

(10) Patent No.: US 8,573,974 B2
(45) Date of Patent: *Nov. 5, 2013

(54) NOZZLE ASSEMBLY FOR LIQUID DROPLET BASED INTERPROXIMAL CLEANER

(75) Inventors: Jozef Johannes Maria Janssen, Herten (NL); Bart Gottenbos, Budel (NL)

(73) Assignee: Koninklijke Philips N.V., Eindhoven (NL)

( * ) Notice: Subject to any disclaimer, the term of this patent is extended or adjusted under 35 U.S.C. 154(b) by 2 days.

This patent is subject to a terminal disclaimer.

(21) Appl. No.: 13/126,208

(22) PCT Filed: Nov. 13, 2009

(86) PCT No.: PCT/IB2009/054830
§ 371 (c)(1),
(2), (4) Date: Apr. 27, 2011

(87) PCT Pub. No.: WO2010/055434
PCT Pub. Date: May 20, 2010

(65) Prior Publication Data
US 2011/0207077 A1 Aug. 25, 2011

Related U.S. Application Data

(60) Provisional application No. 61/115,186, filed on Nov. 17, 2008.

(51) Int. Cl.
*A61C 3/025* (2006.01)

(52) U.S. Cl.
USPC .......................................................... 433/88

(58) Field of Classification Search
USPC ............... 433/80, 84, 85, 88, 89, 98; 604/30, 604/93.01, 131, 140, 147, 149, 151, 186, 604/207, 246; 222/372, 630, 635; 601/160–163, 165, 169; 137/205.5, 137/206; 261/64.3, 78.2; 239/303, 310, 239/311, 337, 340, 341, 353
See application file for complete search history.

(56) References Cited

U.S. PATENT DOCUMENTS 2,757,667 A * 8/1956 Bronk ...................... 128/200.14
3,618,709 A * 11/1971 Boelkins ...................... 184/6.4
3,739,951 A * 6/1973 Geller et al. ................. 222/630

(Continued)

FOREIGN PATENT DOCUMENTS

GB 2302285 A 1/1997
WO 2008012707 A2 1/2008

*Primary Examiner* — Heidi M Eide
*Assistant Examiner* — Justin O'Donnell

(57) ABSTRACT

The cleaning apparatus includes a source of gas under pressure (12) and a source of fluid (14), along with associated gas (26) and fluid (34) chambers, adapted for successive single uses. A user-operated metered valve (22) connects the gas reservoir to the gas chamber, while a liquid pump (30) and a one-way valve (32) connects the liquid reservoir to the liquid chamber. When gas is released from the gas reservoir, it expands rapidly from the valve into the gas chamber, resulting in pressure therein sufficient to open a one-way valve (38) connecting the gas chamber to the liquid chamber. The gas in the liquid chamber forces liquid therein through a liquid line (15) to a connecting point with a gas stream line (13) from the gas chamber. The interaction of the fluid with the gas stream results in a spray of liquid droplets (17) which are directed out of the gas stream line exit orifice (16) to the teeth for cleaning.

9 Claims, 1 Drawing Sheet

(56) References Cited

U.S. PATENT DOCUMENTS

| | | | |
|---|---|---|---|
| 4,149,315 A | 4/1979 | Page, Jr. et al. | |
| 5,820,373 A * | 10/1998 | Okano et al. | 433/80 |
| 6,689,078 B1 | 2/2004 | Rehkemper et al. | |
| 2003/0027100 A1 | 2/2003 | Grant | |
| 2003/0106551 A1 * | 6/2003 | Sprinkel et al. | 128/203.16 |

* cited by examiner

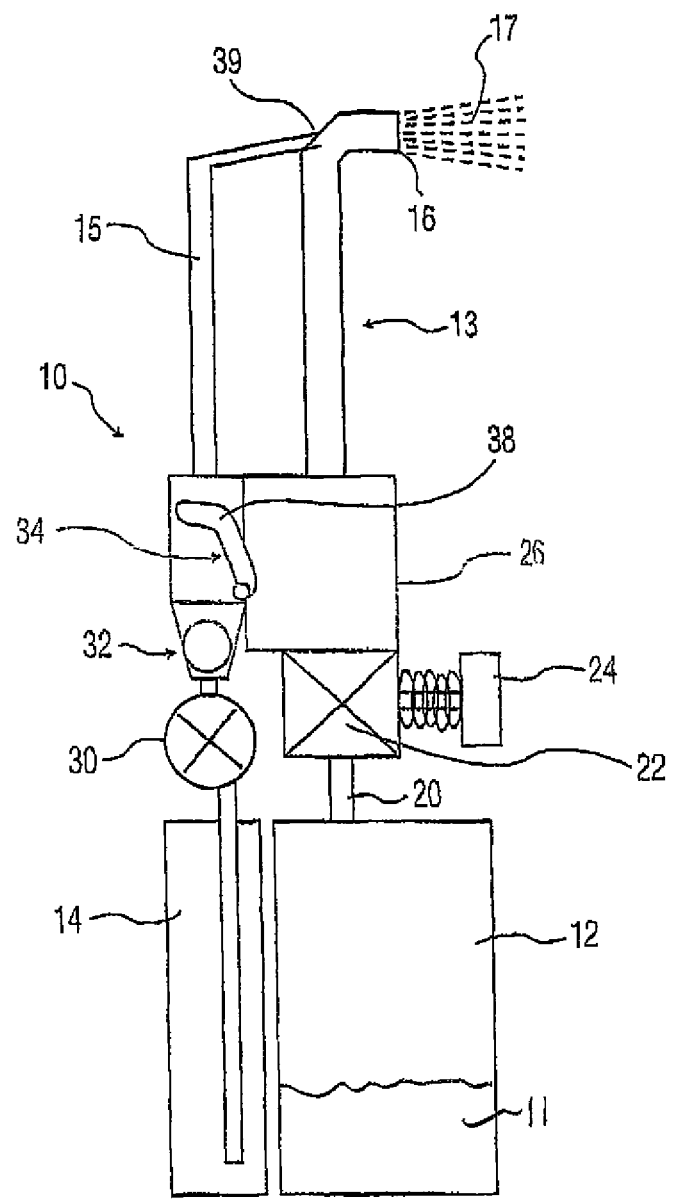

NOZZLE ASSEMBLY FOR LIQUID DROPLET BASED INTERPROXIMAL CLEANER

TECHINICAL FIELD

This invention relates generally to liquid droplet interproximal cleaning devices, and more specifically concerns an assembly for injecting liquid into a gas stream to produce the liquid droplets.

BACKGROUND OF THE INVENTION

The use of gas assisted devices to produce a stream of liquid droplets for use in oral care, i.e. teeth cleaning, is generally known. Such devices are particularly effective for interproximal, i.e. interdental, cleaning as an alternative to flossing, which is problematic for many users. In operation of such devices, however, the breakup of a fluid stream into droplets by interaction with the gas stream is often chaotic and difficult to fully predict and control. Further, there is typically significant energy loss in the system due to inefficiencies in transporting the fluid droplets by the gas stream from their point of generation to the outlet/orifice of the nozzle portion of the device. The volume of gas required for droplet transportation increases the total amount of gas needed, without that volume of gas contributing directly to the effectiveness of droplet cleaning, thereby reducing the usage time of the device for a given amount of gas.

Hence, it is desirable to have a more efficient and effective system for producing fluid droplets using a gas stream.

SUMMARY OF THE INVENTION

Accordingly, an oral care cleaning apparatus for cleaning teeth using liquid droplets is disclosed herein, comprising: a reservoir of compressed gas; a reservoir of liquid; a gas chamber and a one-way metered valve for selectively permitting a selected amount of gas into the gas chamber from the gas reservoir; a liquid chamber to which an amount of liquid is moved; a one-way valve connecting the gas chamber and the liquid chamber, such that when the gas in the gas chamber, expanding as it leaves the metered valve, reaches a certain pressure, the one-way connecting valve opens, permitting a small amount of gas into the liquid chamber to move the liquid therein along a liquid connecting line from the liquid chamber; and a gas line extending from the gas chamber, terminating in an exit orifice, wherein the liquid connecting line connects with the gas line prior to the exit orifice, resulting in a stream of liquid droplets when the liquid encounters the stream of gas, the resulting droplets exiting from the gas line at the exit orifice.

BRIEF DESCRIPTION OF THE DRAWINGS

The drawing is a schematic view of an interproximal cleaning appliance including a nozzle assembly which is the subject of this application.

DETAILED DESCRIPTION OF THE INVENTION

The FIGURE shows a fluid droplet interproximal teeth cleaning appliance/apparatus, generally at 10. The appliance includes a gas reservoir 12 which can contain compressed gas such as $CO_2$ or other gas. The compressed gas 11 in reservoir 12 could also be in a liquid state or a combination of liquid or gas. The reservoir is typically in the form of a replaceable cartridge. The teeth cleaning appliance 10 also includes a liquid reservoir 14 which can contain water or other liquid, including mouthwash or other oral treatment solutions. In general operation, a high velocity gas stream present in a gas stream line 13 (produced as described below) interacts with fluid present in liquid connecting line 15 to produce a spray of liquid droplets 17 which exit the apparatus at a nozzle orifice 16, directed toward the interproximal or other areas of the teeth for cleaning. The user positions the nozzle orifice within the mouth such that the liquid droplets impact the desired area of the teeth. Generally, the liquid droplets will be traveling at a velocity in the range of 60 m/s as they exit from the orifice 16, and with a size in the range of 0.1 to 50 microns.

In more detail, extending from gas reservoir 12 is a small connecting line 20 which connects to a metering valve 22 which is controlled by a user-operated button or similar element 24. The metering valve holds a volume of gas for a single use. The gas exiting from metering valve 22 as it expands is directed to a gas chamber 26. Typically, in the embodiment shown, each operation of button 24 by an operator will produce a burst of gas with a volume of approximately 10 ml, although this amount can vary.

Liquid in reservoir 14 is moved by a pump 30 through a one-way valve 32 to a liquid chamber 34. Liquid pump 30 can be operated separately by a user, independently of the release of gas, or the pump can be connected to be responsive to the operation of button 24 by a user as well, i.e. gas can be moved into chamber 26 and fluid can be pumped into liquid chamber 34 by a user's single action. A single use of liquid is approximately 0.1 ml.

As indicated above, gas from reservoir 12 will expand as it moves into metering valve 22 and then chamber 26. The expanding gas will produce a pressure in chamber 26. The expanding gas will produce increased pressure in chamber 26. The increasing pressure will open a one-way valve 38 which connects gas chamber 26 and liquid chamber 34. In the embodiment shown, this pressure will be about 10 bar. A small amount of gas (approximately 1%) in gas chamber 26 will move through valve 38 into liquid chamber 34, forcing liquid therein through liquid connecting line 15 to a connecting point 39 with gas stream line 13. Typically, the liquid line will have an internal diameter of 250 μm to 1 mm, while the gas line will have a diameter of approximately 2 mm.

The remainder of the gas in gas chamber 26 from the single use of gas produced by activation of button 24 will stream from chamber 26 through gas stream line 13, which terminates at exit orifice 16. The pressure in the gas stream is typically approximately 10 bar, with a gas velocity in the range of 100-300 m/s. In the embodiment shown, liquid connecting line 15 will meet with gas line 13 at point 39 near nozzle exit orifice 16, typically 1-10 mm away from the orifice.

The moving liquid will intersect the gas stream in line 13, resulting in the generation of liquid droplets in conventional fashion. The resulting droplets will then exit through orifice 16, directed to the dental regions for cleaning. As indicated above, the speed of the droplets typically will be in the range of 60 m/s when they exit orifice 16.

The advantage to the above system is that nearly all the gas in chamber 26 is used to produce the liquid droplets, when liquid in line 15 intersects the gas stream in line 13, with resulting improved efficiency. Since the liquid line connects with the gas line close to the nozzle exit, it is not necessary for the gas stream to transport the liquid droplets for an extended distance. In the embodiment shown, the gas chamber and the liquid chamber with the connecting one-way value are located in what can be referred to as a nozzle portion of the apparatus. However, these members can be located further to the rear of the apparatus, such as in the handle.

Accordingly, a new nozzle system is disclosed which utilizes a small portion of a high pressure gas stream to pressurize a liquid chamber to force liquid therein along a connecting line to a point near the nozzle orifice where it intercepts the gas stream, which is moving at a high velocity, to produce fine liquid droplets for dental cleaning, particularly interproximal cleaning.

Although a preferred embodiment of the invention has been disclosed for purposes of illustration, it should be understood that various changes, modifications and substitutions may be incorporated in the embodiment without departing from the spirit of the invention which is defined by the claims which follow.

The invention claimed is:

1. An oral care cleaning apparatus adapted for successive single uses for cleaning teeth using liquid droplets, comprising:
   a reservoir of compressed gas (12);
   a reservoir of liquid (14);
   a gas chamber (26) separate from the reservoir of compressed gas and a one-way metered valve (22) for selectively holding and permitting a selected amount of compressed gas for a single cleaning use into the gas chamber from the compressed gas reservoir;
   a liquid chamber (34) separate from the reservoir of liquid to which an amount of liquid is moved from the reservoir of liquid, including a connecting line therefrom;
   a one-way valve (38) connecting the gas chamber and the liquid chamber, such that when the compressed gas in the compressed gas chamber, expanding as it leaves the one-way metered valve, reaches a certain pressure, the one-way connecting valve opens, permitting a small amount of compressed gas from the selected amount of compressed gas into the liquid chamber to move a single use of liquid therein along the connecting line (15) from the liquid chamber;
   a gas line (13) separate from the connecting line extending from the gas chamber, terminating in an exit orifice (16), wherein the connecting line connects with the gas line prior to the exit orifice, resulting in a stream of liquid droplets for a single use when the amount of liquid encounters a remainder part of the selected amount of compressed gas in the gas line, the resulting stream of liquid droplets exiting from the gas line at the exit orifice; and
   a control member which when operated permits a single use of gas to move into the one-way metered valve and then into the gas chamber and also results in a single use of liquid being moved into the liquid chamber.

2. The oral care cleaning apparatus of claim 1, wherein the connecting line connects with the gas line at a point within the range of 1-10 mm from the exit orifice.

3. The oral care cleaning apparatus of claim 1, wherein the compressed gas in the compressed gas reservoir is in a gaseous state.

4. The oral care cleaning apparatus of claim 1, wherein the compressed gas in the compressed gas reservoir is in a liquid state or a combination of liquid and gas.

5. The oral care cleaning apparatus of claim 1, wherein the one-way metered valve receives a defined volume of gas upon operation thereof by a user.

6. The oral care cleaning apparatus of claim 5, wherein the defined volume of gas is approximately 10 ml from the exit orifice.

7. The oral care cleaning apparatus of claim 1, including a pump (30) and a one-way valve (32) between the liquid reservoir and the liquid chamber, wherein operation of the pump results in a single use volume of liquid being moved into the liquid chamber.

8. The oral care cleaning apparatus of claim 1, wherein the small amount of gas directed into the liquid chamber to move the liquid through the connecting line for a single use of the apparatus is approximately 1% of the selected amount of gas.

9. The oral care cleaning apparatus of claim 1, wherein the selected amount of gas for a single use is approximately 10 ml, and wherein the amount of liquid is approximately 0.1 ml, suitable for a single use.

* * * * *